United States Patent [19]

Stein

[11] Patent Number: 4,883,682

[45] Date of Patent: Nov. 28, 1989

[54] PROCESS FOR THE PREPARATION OF A STERILIZED CASEIN-BASED LIQUID COMPOSITION

[75] Inventor: Jehuda Stein, Bremgarten, Switzerland

[73] Assignee: Nestec S.A., Vevey, Switzerland

[21] Appl. No.: 198,234

[22] Filed: May 25, 1988

[30] Foreign Application Priority Data

Jun. 9, 1987 [CH] Switzerland .................. 2165/87

[51] Int. Cl.$^4$ .................. A23C 7/04; A23C 9/15; A23L 1/29
[52] U.S. Cl. .................. 426/580; 426/424; 426/585
[58] Field of Search .................. 426/580, 585, 424, 74, 426/40

[56] References Cited

U.S. PATENT DOCUMENTS

| | | | |
|---|---|---|---|
| 4,055,555 | 10/1977 | Badertscher | 426/657 |
| 4,091,120 | 5/1978 | Goodnight, Jr. et al. | 426/656 |
| 4,192,901 | 3/1980 | Yasumatsu et al. | 426/580 |
| 4,397,927 | 8/1983 | Brog | 426/585 |

Primary Examiner—Donald E. Czaja
Assistant Examiner—Helen Pratt
Attorney, Agent, or Firm—Vogt & O'Donnell

[57] ABSTRACT

In the process, an aqueous 10 to 18% by weight suspension of casein and an aqueous 10 to 30% by weight suspension of KOH or NaOH and Ca(OH)$_2$ are prepared so as to obtain a KOH content of from 4 to 11 g/kg or an NaOH content of from 2.5 to 8 g/kg casein dry matter and a Ca(OH)$_2$ content of from 14 to 20 g/kg casein dry matter, the two suspensions are mixed to give a solution of mixed K/Ca or Na/Ca caseinate having a pH value below 6.5, the mixture is heat-treated and cooled, fats are introduced and homogenized, followed by other additives, after which the product is sterilized, homogenized and packed aseptically in suitable packs.

6 Claims, No Drawings

PROCESS FOR THE PREPARATION OF A STERILIZED CASEIN-BASED LIQUID COMPOSITION

BACKGROUND OF THE INVENTION

This invention relates to a process for the preparation of a sterilized liquid composition based on casein, more especially a composition adapted for oral or enteral administration.

For the preparation of a sterilised, casein-based enteral composition having a shelf life of up to 12 months, due to the presence of casein, the composition has to be heat-treated for at least 3 minutes at 130° C. This is because the heat-resistant proteases in milk precipitate with acidic casein during its preparation at the isoelectric point (pH 4.6). Because these proteases are not totally deactivated by heat treatment, they cause proteolytic degradation of the casein and leave the end product with a bitter taste, causing it to coagulate after storage for 2 to 6 months. This proteolytic degradation of the casein depends on the concentration of protease in the casein used. Now, a conventional ultra-high-temperature (UHT) treatment of the casein, i.e., for 3 to 5 seconds at 148 or 150° C., which is sufficient to guarantee complete sterility, it not sufficient for completely inactivating the small quantities of residual protease which are difficult to detect by analytical techniques. Accordingly, a more severe heat treatment, i.e., 5 minutes at 130° C., has to be applied. However, a heat treatment as severe as this results in the formation of lysinoalanine (LAL) in a quantity of up to 1800 mg/kg protein and in blockage of the lysine by as much as 20%. The presence of high concentrations of lysinoalanine (LAL) can pose problems of toxicity while blockage of the lysine results in a nutritional loss.

Accordingly, the object of the present invention is to provide a process for the preparation of a sterilized caseinbased composition in which the proteases are deactivated, containing only very low concentrations of LAL (150 to 170 mg/kg protein), and where there is no blockage of the lysine.

This object is achieved by the process according to the invention.

DESCRIPTION OF THE INVENTION

The present invention relates to a process for the preparation of a sterilised liquid composition based on acidic casein, in which a 10 to 18% by weight aqueous suspension of casein and a 10 to 30% by weight suspension of KOH or NaOH and Ca(OH)$_2$ are prepared so as to obtain a KOH content of from 4 to 11 g/kg or an NaOH content of from 2.5 to 8 g/kg casein dry matter and a Ca(OH)$_2$ content of from 14 to 20 g/kg casein dry matter, the two suspensions are mixed to give a solution of mixed K/Ca or Na/Ca caseinate having a pH below 6.5, the mixture is heat-treated and cooled, fats are introduced and homogenized, followed by the other additives, after which the product is sterilized, homogenized and packed aseptically in suitable packs.

The heat treatment of the caseinate is carried out for 5 minutes at approximately 130° C., cooling takes place at 60 to 80° C. and the sterilization of the end product by UHT is effected for 5 seconds at around 148° C.

The casein suspension is prepared at a pH value of approximately 4.6 and at a temperature of from 10 to 65° C. The object of adding KOH or NaOH and Ca(OH)$_2$ is to adjust the pH of the final solution before the heat treatment which should not exceed 6.5. This is because it has been found that, at this pH, the formation of LAL is minimal during the subsequent heat treatment. The potassium caseinate is soluble in water whereas the calcium caseinate is not. When the two suspensions of casein (acidic) and KOH or NaOH + Ca(OH)$_2$ (alkaline) are combined, they give a stable colloidal solution although the calcium caseinate is sparingly soluble in water.

Effective adjustment of the ratio by weight of KOH or NaOH to Ca(OH)$_2$ avoids any precipitation of calcium caseinate during the heat treatment, thus guaranteeing the preparation of a product in which no deposits are formed for at least 12 months.

On the other hand, the direct addition of Ca ions in the form of calcium caseinate makes it unnecessary or less important separately to add Ca in the form of insoluble salts, such as Ca(OH)$_2$, CaCo$_3$ or Ca citrate, which could cause deposits to be formed during storage, or in the form of soluble salts, such as CaCl$_2$, which might lead to proteinic coagulation during heating. Since calcium caseinate on its own is sparingly soluble in water and is not heat-resistant, the preparation of heat-resistant mixed Ca/K or Ca/Na caseinate makes it possible to solve the problem of deposits in the pack in the event of prolonged storage for up to 12 months.

A 10 to 13% by weight acidic casein suspension and a 10% by weight KOH or NaOH and Ca(OH)$_2$ suspension are normally prepared in accordance with the invention.

The other additives which are added after addition of fats are carbohydrates, soluble mineral salts, such as potassium citrate, magnesium chloride, sodium phosphate, potassium hydroxide, sodium citrate, sodium chloride, if necessary calcium hydroxide, oligoelements and vitamins.

The addition of the carbohydrates least of all makes it possible to avoid the blockage of lysine which would occur if the carbohydrates were present during the first heat treatment.

EXAMPLES

The rest of the description is given with reference to the Examples which relate more especially to the preparation of compositions for enteral administration. The percentages are by weight.

EXAMPLE 1

To obtain 1000 kg of end product, on the one hand a suspension of 42 kg of acidic casein (corresponding to 39 kg of dry matter) in 400 l water and, on the other hand, a suspension of 298 g of KOH and 700 g of Ca(OH)$_2$ in 9 liters water are prepared. These two suspensions are mixed to give a solution of mixed K/Ca caseinate having a pH of 6.48. The mixture is preheated to 80° C. and then treated for 5 minutes at 130° C., followed by sudden cooling to 80° C. The pH is then 6.54, the fats heated to 60° C. containing the liposoluble vitamins are dosed into the mixture which is then homogenized. After cooling to 10° C., carbohydrates (maltodextrin and glucose syrup), mineral salts, water-soluble vitamins and oligoelements are added. The mixture is subjected to a UHT treatment, namely preheating to 80° C., steam-heating for 5 seconds to 148° C. and then sudden cooling to 80° C. The product is then homogenized again, cooled in an aseptic system to 20° C. and introduced into a sterile container before finally arriving at an aseptic filling line. Analysis of the end products produces the following results:

| | | |
|---|---|---|
| pH of the composition | 6.72 | |
| dry matter % | 19.75 | |
| fats % | 3.39 | |
| proteins % | 3.78 | |
| carbohydrates % | 12.1 | |
| ash % | 0.48 | |
| Na | 47 | |
| K | 121 | |
| Ca | 47 | |
| Mg | 23 | mg/100 g |
| P | 48 | |
| Cl | 95 | |
| reactive lysine content | 7.83 | g/16 g N |

The LAL content is 150–170 mg/kg protein while the blocked lysine content is so low that it cannot be detected. No deposit is detected after storage for 12 months. No change in structure is observed.

EXAMPLE 2

To obtain 1000 kg of end product, on the one hand a suspension of 42 kg acidic casein (corresponding to 39 kg of dry matter) in 400 liters water and, on the other hand, a suspension of 213 g of KOH and 700 g of Ca(OH)$_2$ in 9 litres water are prepared. The two suspensions are mixed to give a solution having a pH of 6.37. The pH of the solution after treatment for 5 minutes at 130° C. is 6.41. The remaining treatment of this mixture is the same as in Example 1. Analysis of the end product produces the following results:

| | | |
|---|---|---|
| pH of the composition | 6.73 | |
| dry matter % | 21.75 | |
| fats % | 3.36 | |
| proteins % | 6.32 | |
| carbohydrates % | 11.5 | |
| ash % | 0.60 | |
| Na | 41 | |
| K | 151 | |
| Ca | 60 | |
| Mg | 31 | mg/100 g |
| P | 59 | |
| Cl | 97 | |
| Reactive lysine content | 7.53 | g/16 g N |

The LAL content is low (160 mg/kg protein) while the blocked lysine content is so low that is cannot be detected. No deposit is detected after storage for 12 months. There is no change in structure after 12 months.

EXAMPLE 3

To obtain 1000 kg of end product, on the one hand a suspension of 78.7 kg of acidic casein (corresponding to 72.8 kg of dry matter) in 400 l water and, on the other hand, a suspension of 553 g of KOH and 1000 g of Ca(OH)$_2$ in 12 liters water are prepared. The two suspensions are mixed to give a solution having a pH value of 6.18. The pH of the solution after treatment for 5 minutes at 130° C. is 6.17. The remaining treatment of this mixture is the same as in Example 1.

Analysis of the end product gives the following results:

| | |
|---|---|
| pH of the composition | 6.39 |
| protein content | 6.32% |
| reactive lysine content | 7.36 g/16 g N |

The LAL content is low (150 mg/kg protein) while the blocked lysine content is so low that it cannot be detected. No deposit is detected after storage for 12 months, nor is any change in structure observed.

EXAMPLE 4

To obtain 100 kg of end product, on the one hand a suspension of 78.7 kg of acidic casein in 400 liters water and, on the other hand, a suspension of 425 g of KOH and 1000 g of Ca(OH)$_2$ in 12 liters water are prepared. The two suspensions are mixed to give a solution having a pH of 6.12. The pH of the solution after treatment for 5 minutes at 130° C. is 6.11.

The remaining treatment of this mixture is the same as in Example 1.

Analysis of the end product produces the following results:

| | |
|---|---|
| pH of the composition | 6.33 |
| protein content | 6.32% |
| reactive lysine content | 7.36 g/16 g N |

The LAL content is low (150 mg/kg protein) while the blocked lysine content is so low that it cannot be detected. No deposit is detected after storage for 12 months, nor is any change in structure observed.

I claim:

1. A process for the production of a sterilized liquid composition based upon acidic casein comprising:
preparing and mixing a 10% to 18% by weight aqueous suspension containing acidic casein and a 10% to 30% by weight aqueous suspension containing Ca(OH)$_2$ and containing a substance selected from a group consisting of KOH and NaOH for obtaining a solution having a pH below 6.5 and wherein the Ca(OH)$_2$ content is from 14 g/kg to 20 g/kg casein dry matter, and wherein when KOH is the substance, the KOH content is from 4 g/kg to 11 g/kg dry matter and wherein when NaOH is the substance, the NaOH content is from 2.5 g/kg to 8 g/kg casein dry matter;
heat-treating the solution;
cooling the heat-treated solution;
introducing and then homogenizing fats into the cooled solution;
introducing additives including carbohydrates into the homogenized solution for preparing a product mixture;
sterilizing the mixture;
homogenizing the sterilized mixture; and
packaging the homogenized mixture aseptically.

2. A process according to claim 1 wherein the solution is heat-treated for about 5 minutes at about 130° C., then heat-treated solution is cooled to from 60° C. to 80° C. and the mixture is sterilized by UHT for 5 seconds at about 148° C.

3. A process according to claim 1 wherein a 10% to 13% by weight aqueous suspension of acidic casein is prepared.

4. A process according to claim 1 wherein a 10% by weight KOH and Ca(OH)$_2$ suspension is prepared.

5. A process according to claim 1 wherein a 10% by weight NaOH and Ca(OH)$_2$ suspension is prepared.

6. A process according to claim 1 wherein the additives further include, soluble mineral salts and vitamins.

* * * * *

UNITED STATES PATENT AND TRADEMARK OFFICE
CERTIFICATE OF CORRECTION

PATENT NO. : 4,883,682

DATED : November 28, 1989

INVENTOR(S) : Jehuda STEIN

It is certified that error appears in the above-identified patent and that said Letters Patent is hereby corrected as shown below:

Column 4, line 10, "100" should be --1000--.

Column 4, line 42 (line 12 of claim 1), after "g/kg", insert --casein--.

Column 4, line 57 (line 3 of claim 2), "then" should be --the--.

Signed and Sealed this

Eighteenth Day of September, 1990

Attest:

HARRY F. MANBECK, JR.

*Attesting Officer*       *Commissioner of Patents and Trademarks*